(12) United States Patent
Wind

(10) Patent No.: US 9,345,799 B1
(45) Date of Patent: May 24, 2016

(54) SYSTEM FOR STERILIZING WRITING INSTRUMENTS

(71) Applicant: Brian E. Wind, North Canton, OH (US)

(72) Inventor: Brian E. Wind, North Canton, OH (US)

( * ) Notice: Subject to any disclaimer, the term of this patent is extended or adjusted under 35 U.S.C. 154(b) by 0 days.

(21) Appl. No.: 14/631,876

(22) Filed: Feb. 26, 2015

(51) Int. Cl.
*A61L 2/10* (2006.01)
*B43K 23/02* (2006.01)
*B43K 7/00* (2006.01)

(52) U.S. Cl.
CPC . *A61L 2/10* (2013.01); *B43K 7/005* (2013.01); *B43K 23/02* (2013.01)

(58) Field of Classification Search
CPC ............ A61L 2/10; A61L 2/24; B43K 23/00; B43K 23/001; G01B 5/28; G01D 9/36
USPC ......... 250/455.11, 504 R; 422/186.3, 121, 24
See application file for complete search history.

(56) References Cited

U.S. PATENT DOCUMENTS

| | | | | |
|---|---|---|---|---|
| 1,401,454 A * | 12/1921 | Andersen | ............... | B43K 23/00 40/334 |
| 2,665,187 A * | 1/1954 | Kinley | ..................... | G01B 5/28 33/542 |
| 6,190,078 B1 * | 2/2001 | Smith | .................. | B43K 23/001 401/131 |
| 6,392,639 B1 * | 5/2002 | Lee | ........................ | G06F 1/1626 178/19.01 |
| 8,058,629 B2 * | 11/2011 | Long | ........................ | A61L 2/10 250/455.11 |
| 8,357,914 B1 * | 1/2013 | Caldwell | .................. | A61L 2/10 250/455.11 |
| 2006/0175554 A1 * | 8/2006 | Riddell | ..................... | A61L 2/10 250/455.11 |
| 2012/0074334 A1 * | 3/2012 | Milligan | ................... | A61L 2/10 250/455.11 |
| 2013/0277574 A1 * | 10/2013 | Dayton | ..................... | A61L 2/10 250/455.11 |

\* cited by examiner

*Primary Examiner* — David A Vanore
(74) *Attorney, Agent, or Firm* — Lech Law, LLC; Robert R. Lech

(57) ABSTRACT

A writing instrument sterilizer system is disclosed. The system comprises a writing instrument, wherein the surface of the writing instrument forms at least one alignment indentation. The system further comprises a sterilizer comprising an illumination source, a collection frame, a discharge frame and a transport mechanism to transport the writing instrument between the collection frame and the discharge frame. At least a portion of the sterilizer comprises at least one alignment protrusion configured to cooperate with the at least one alignment indentation formed by the surface of the writing instrument.

10 Claims, 3 Drawing Sheets

SYSTEM FOR STERILIZING WRITING INSTRUMENTS

TECHNICAL FIELD

The present application relates generally to sterilization and dispensing devices for writing instruments, and more particularly to an ultra violet (UV) light writing instrument sterilizer including a receiving and dispensing mechanism, and to the writing instrument compatible with the sterilizer.

STATEMENT REGARDING FEDERALLY SPONSORED RESEARCH

No government monies were used in the development of the subject matter of this application.

BACKGROUND

Hand-held writing devices are commonly utilized and shared by individuals in public places such as hospitals, doctor's offices, banks, department stores, and restaurants. Infectious microorganisms including viruses and bacteria colonize on these writing devices and promote the spread of communicable diseases from the common cold to more serious infections. The use of ultraviolet light for its purification germicidal effects is well known. When administered at the desired frequencies, durations, and intensities, ultraviolet light is able to kill a wide spectrum of microorganisms.

While prior art sterilization devices are known, mechanisms for transporting writing instruments through a field of ultraviolet light occasionally malfunction. For example, one or more writing instruments can become misaligned within a sterilizer causing the writing instruments within to jam. Accordingly, there is a need for improved mechanisms within a sterilization device for receiving, aligning, transporting and dispensing writing instruments.

SUMMARY

According to a first aspect of the present application, an example writing instrument sterilizer system is disclosed. The example system comprises a writing instrument and a writing instrument sterilizer. The surface of the writing instrument forms at least one alignment indentation to engage and cooperate with a corresponding alignment protrusion within the writing instrument sterilizer.

The writing instrument sterilizer comprises a collection frame configured to receive the writing instrument, a discharge frame configured to dispense the writing instrument, a transport mechanism configured to transport the writing instrument from the collection frame to the discharge frame, and an illumination source that sterilizes the writing instrument by emitting radiation to the surface of the writing instrument. The sterilizer further comprises at least one alignment protrusion that engages and cooperates with the at least one alignment indentation of the writing instrument to maintain alignment of the writing instrument within the sterilizer.

According to a second aspect of the present application, an example writing instrument is disclosed. The example writing instrument is for use in a sterilizer system, and the example writing instrument comprises a barrel having an outer surface. The outer surface of the barrel forms at least one alignment indentation for cooperating with a writing instrument sterilizer.

An object of the present application is to provide a writing instrument sterilization system having an improved collection and automatic dispensing delivery mechanism. This and other objects, features, and/or advantages may accrue from various aspects of embodiments of the present application, as described in more detail below.

BRIEF DESCRIPTION OF THE DRAWINGS

The accompanying figures, which are incorporated in and constitute a part of the specification, illustrate various example systems, devices methods, and so on, and are used merely to illustrate various example embodiments. Like reference numerals refer to identical or similar components or steps. It should be noted that the various components depicted in the figures may not be drawn to scale, and that the various assemblies and designs depicted in the figures are presented for purposes of illustration only, and should not be considered in any way as limiting.

DETAILED DESCRIPTION

Figure 1:
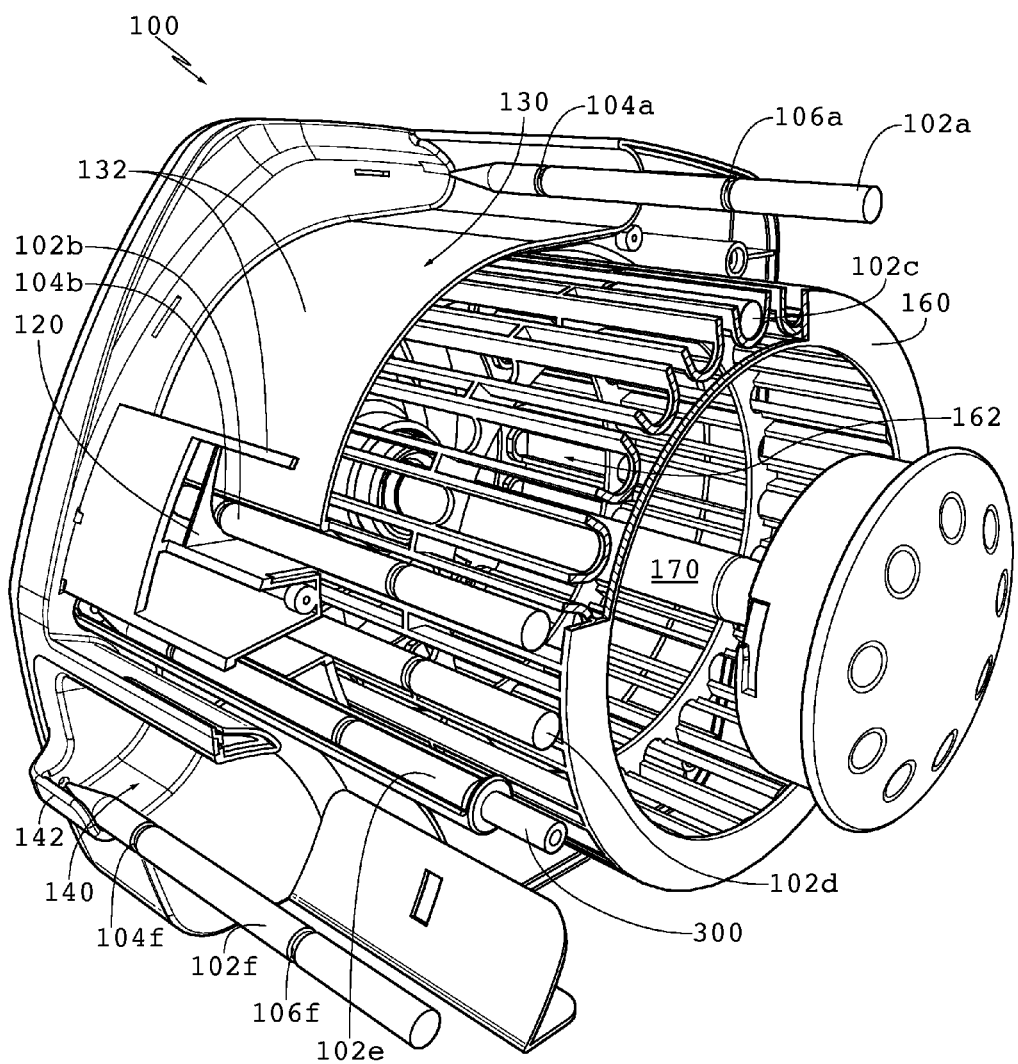
FIG. 1 illustrates a cutaway perspective view of the system in accordance with this application.

Particular embodiments of the present system will now be described in greater detail with reference to the figures. Like reference numerals apply to similar parts throughout the several views.

This system overcomes the conventional problems associated with automated delivery systems, as described above. This is accomplished, in part, using one or more alignment protrusions within a UV light writing instrument sterilizer that engage and cooperate with one or more alignment indentations formed within a writing instrument.

Figure 2:
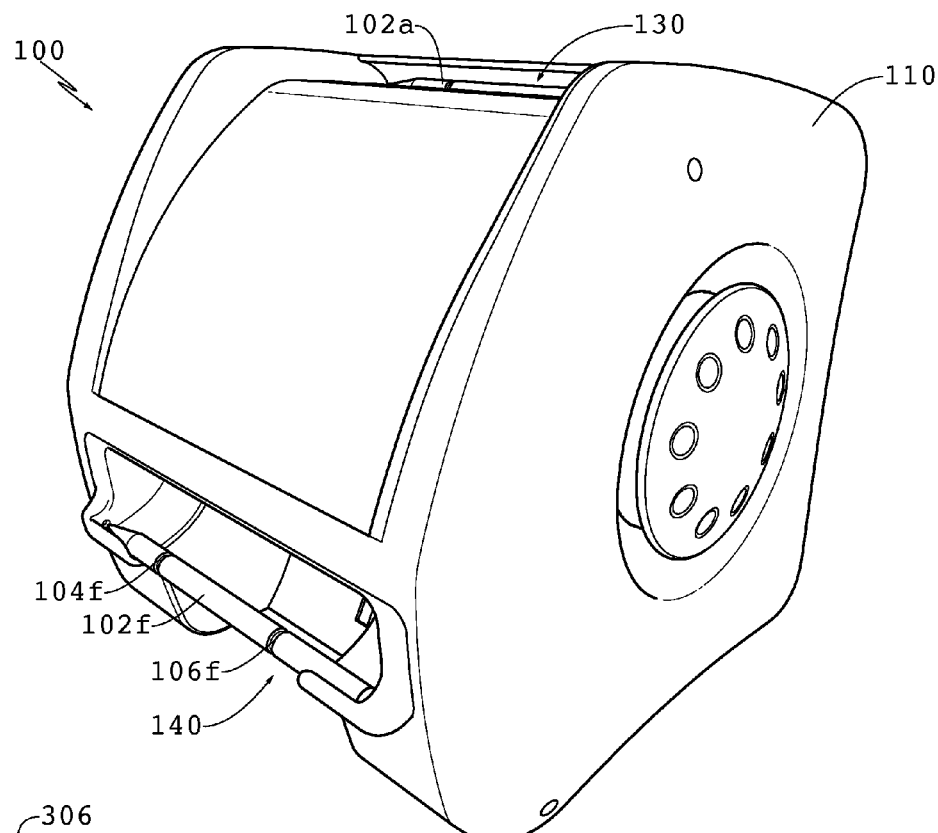
FIG. 2 illustrates a perspective view of the system in accordance with this application.
Figure 3:
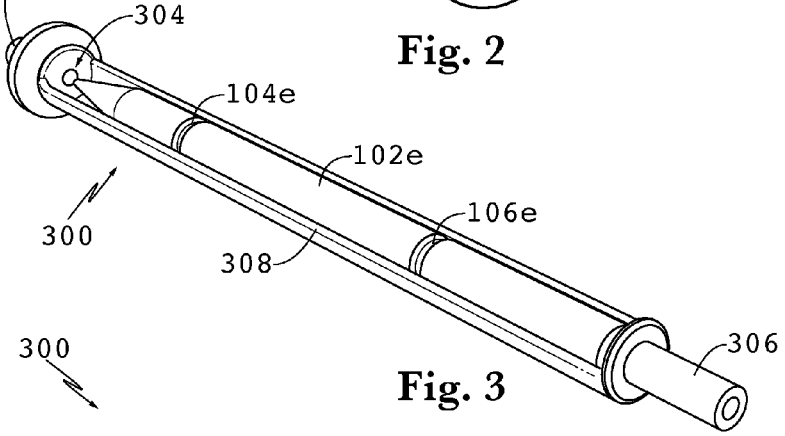
FIG. 3 illustrates a perspective view of an ejector member of the system in accordance with this application.
Figure 4:
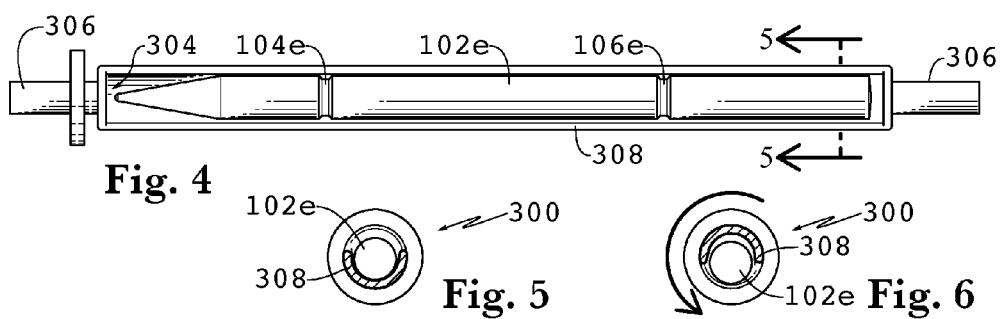
FIG. 4 illustrates a top view of the ejector member in accordance with this application.

FIGS. 1 and 2 illustrate a writing instrument sterilizer 100 for sanitizing a writing instrument having at least one alignment indentation, such as example writing instrument 102a. FIG. 2 depicts an exemplary writing instrument sterilizer 100. Sterilizer 100 defines a collection opening 130 for receiving a writing instrument such as writing instrument 102a, a discharge opening 140 for dispensing a writing instrument such as writing instrument 102f, a housing 110 comprising various panels. The housing 110 is preferably lined with a reflective material (not shown), such as for example, a metallic laminate and/or any other material having suitable reflective properties to reflect the irradiating light from a UV light 170, as shown in FIG. 1, back toward the surfaces of the writing instruments within the writing instrument sterilizer 100 in order to maximize the exposure to the various writing instruments.

As best illustrated with reference to FIG. 1, example writing instrument 102a comprises a barrel having an outer surface. The outer surface of the barrel forms at least one alignment indentation for cooperating with writing instrument sterilizer 100.

Specifically, example writing instrument 102a comprises two alignment indentations 104a and 106a. In the illustrated example embodiment, alignment indentations 104a and 106a are formed circumferentially around the longitudinal axis of the writing instrument. Although the example embodiment depicts alignment indentations 104a and 106b as chamfered channels, the alignment indentations could be embodied as U-shaped, V-shaped, beveled, or square.

The writing instrument sterilizer 100 comprises a collection frame 132 that forms a collection opening 130. The collection frame 132 further forms a guide path that employs gravity to feed a writing instrument into a carousel feeding position and onto a carousel 160. Writing instrument 102a is illustrated in the collection opening 130 and writing instrument 102b is illustrated in the carousel feeding position.

Two alignment protrusions, such as alignment protrusion 120, are formed by collection frame 132 and disposed in the carousel feeding position. The alignment protrusions are spaced apart to engage and cooperate with alignment indentations of a writing instrument such as alignment indentations 104b and 106b of writing instrument 102b. The engagement and cooperation between alignment indentations 104b and 106b and the alignment protrusions of sterilizer 100 ensure that writing instrument 102b will be properly aligned as it is fed into one of a plurality of transport channels formed within a carousel 160. An example of an unoccupied transport channel is shown at reference number 162.

Although the example sterilizer 100 is illustrated with alignment protrusions formed by collection frame 132, alternate embodiments of sterilizer 100 may comprise alignment protrusions in other locations. For example, carousel 160 may form one or more alignment protrusion in each transport channel. In another alternate embodiment, discharge frame 142 may form one or more alignment protrusions that cooperate with alignment indentations 104f and/or 106f.

Carousel 160 is configured to rotate about its central axis, and is further configured, by virtue of the plurality of transport channels formed therein, to transport a writing instrument from the carousel feeding position to a carousel exit position. Writing instrument 102c illustrates a writing instrument that has traveled a portion of the way between the carousel feeding position and the carousel exit position. Writing instrument 102d is depicted in the carousel exit position.

At the carousel exit position, a sterilized writing instrument may be transferred from carousel 160 to an ejector member 300. Ejector member 300, shown in greater detail with respect to FIGS. 3-6, forms an elongated, U-shaped cavity into which a sterilized pen may be transferred. Ejector member 300 is illustrated supporting a writing instrument 102e received from carousel 160.

As shown, writing instrument sterilizer 100 comprises a discharge frame 142 that forms a discharge opening 140. Discharge opening 140 has an elongated shape through which a sterilized writing instrument, such as writing instrument 102e may be dispensed. Discharge frame 142 receives a sterilized writing utensil from ejector member 300 thereby providing a sterilized writing instrument such as writing instrument 102f in the discharge opening 140.

As illustrated in FIGS. 1 and 2, sterilizer 100 comprises a UV light 170 provided to sterilize the writing instruments. Although only one UV light 170 is shown in FIG. 1, it is understood that numerous UV lights 170 may disposed within the sterilizer 100. UV radiation is a form of electromagnetic radiation that contains measurable wavelengths in the 4-400 nanometer range. UV radiation is a well-known sterilization agent. The ultraviolet light is effective at eradicating bacteria, viruses and other pathogens. The exposure to UV light necessary to kill bacteria (or the "kill" factor) is a product of time and intensity. Suitable wavelengths for sterilizing a writing instrument are in the range of 100-300 nanometers. The ideal UV germicidal wavelength is approximately 254 nanometers.

However, it is also understood that exposure to UV light at an intensity necessary for effective and efficient eradication or sterilization of pathogenic agents is harmful to the human body so appropriate protective shielding is utilized within the dispenser to prevent direct or reflected UV light from striking the human body. The UV radiation required to effectively eradicate most pathogenic agents will be an intensity ranging from 1000-100,000 microwatts/cm2 with an ideal range of 3,000-10,000 microwatts/cm2. The object of this invention is to effectively eradicate pathogens or micro-organisms by exposing all surfaces of the writing instrument to direct (or reflected) exposure or contact with the UV radiation for a sufficient period of time. According to this exemplary embodiment, a predetermined time period for applying UV radiation to effectively sterilize the writing instruments 8 has been calculated in the range of 30-240 seconds. Ideally, the UV radiation exposure time period when using a UV light with a wavelength of approximately 254 nanometers at an intensity of 10,000 microwatts/cm2 is in the range of 80-110 seconds. However, the time may vary based on the internal surface area, the internal reflective material used, and the radiation level and/or wattage output of the UV lamp 170.

Various types of illumination lamps may be employed, such as for example, an UV light, a pulsed or flashed UV light, a germicidal UV flash light or LED (light emitting diodes), pulsed UV and/or any other disinfecting illumination source now known or later discovered in accordance with this invention. Ideally, the present invention will include a UV lamp which produces UV light wavelengths of approximately 254 nanometers.

To ensure that only one writing instrument is permitted to exit the discharge opening 140 at one time, the present invention includes single writing instrument ejector member 300. As shown in FIGS. 3-6, the ejector member 300 includes an elongated, U-shaped body 308 secured to and extending parallel to an axis of a pivot rod 306 at either end.

Figure 5:
FIG. 5 illustrates a cross-sectional view of the ejector member in a first writing instrument receiving position in accordance with this application.

The body 308 of ejector member 300 forms a cavity 304 just large enough to permit entry of a single writing instrument, such as writing instrument 102e, within cavity 304 when the ejector member 300 is in a first writing instrument receiving position, illustrated by FIG. 5. In the first writing instrument receiving position, ejector member 300 receives a writing instrument as it exits carousel 160 at the carousel exit position.

Figure 6:
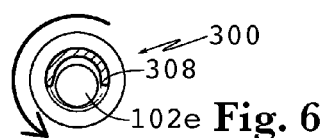
FIG. 6 illustrates a cross-sectional view of the ejector member in a second writing instrument discharging position in accordance with this application.

Before carousel 160 rotates such that a successive transport channel carrying a writing instrument reaches the carousel exit position, the ejector member 300 is rotated into a second writing instrument discharging position, illustrated by FIG. 6. The rotation of ejection member 300 from the first position to the second position causes any writing instrument supported within cavity 304, such as writing instrument 102e, to drop onto the discharge frame 142 and subsequently proceed to the bottom of the discharge opening 140 where it is presented to a user. Ejector member 300 is then rotated back to the first writing instrument receiving position to receive another writing instrument from carousel 300.

Figure 7:
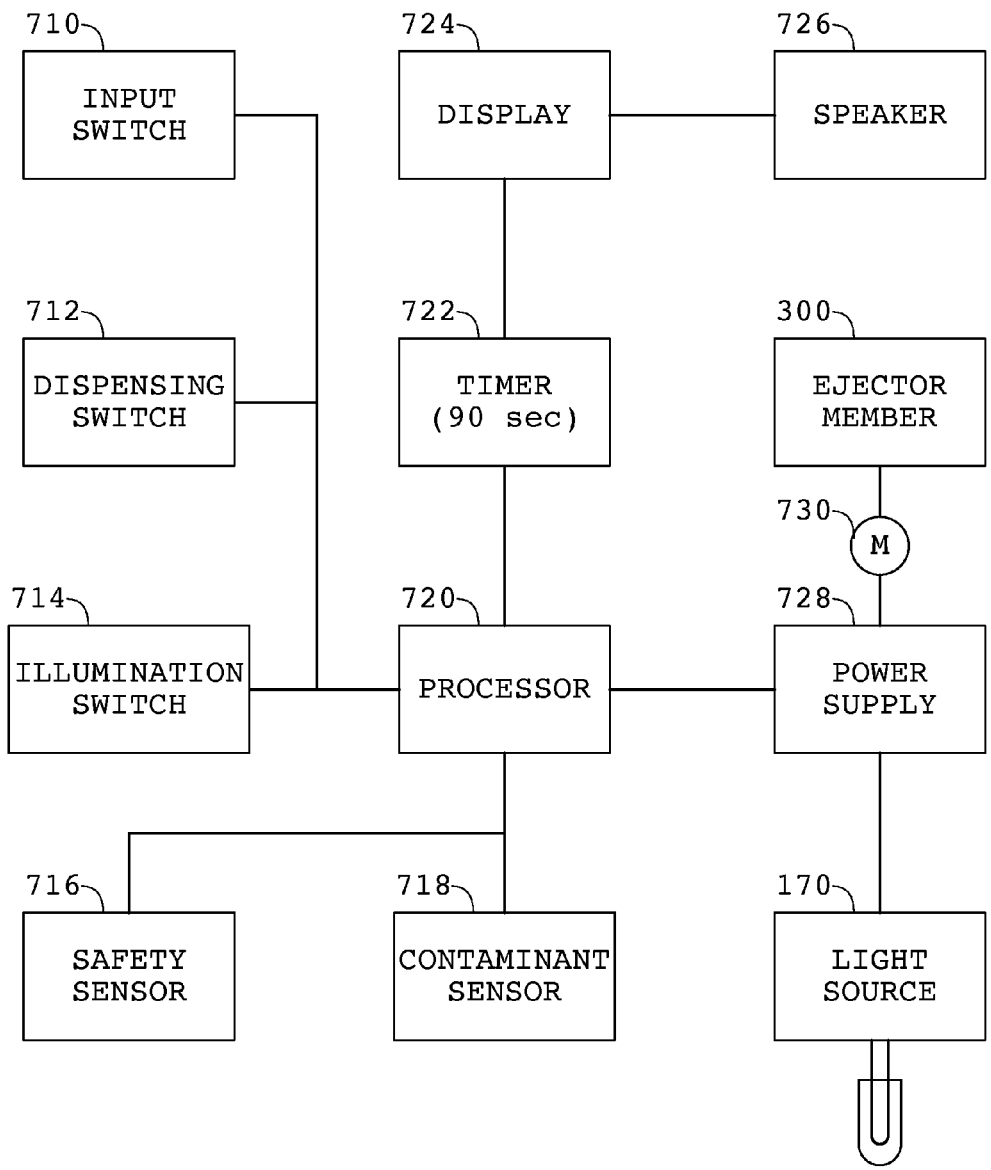
FIG. 7 illustrates a control circuit for the writing instrument sterilizer in accordance with this application.

FIG. 7 illustrates a control circuit for the writing instrument sterilizer 100 according to this invention. In operation, a user may insert a writing instrument such as writing instrument 102a into the collection opening 130. An input switch input switch 710 may be located at the opening of the collection opening 130. When the writing instrument 102a is inserted into the collection opening 130, a processor 720 receives a signal indicating the receipt of a new writing instrument 102a. The processor 720 transmits a control signal to the power supply 728 to provide a source of power to the UV light 170 thereby allowing the various writing instruments within the writing instrument sterilizer 100 to be sterilized by the irradiating UV light 170.

Within the control circuit, the writing instrument sterilizer 100 may include a timer 722 to measure a predetermined period of time that the UV light 170 irradiates the writing instrument 102a. A preferred predetermined period of time has been determined to be approximately 90 seconds in accordance with this exemplary embodiment. However, it is to be understood that the predetermined time may vary based on a variety of different parameters, such as the UV light bulb, the size of the housing, the reflective properties of the inner housing surfaces, the design of the carousel 160, the writing instruments within the housing 110 and/or other variables.

The timer 722 may be connected to a display 724 or speaker 726. When the writing instrument 102a has been sufficiently sterilized a visual notification may be displayed on display 724 and/or an audible sound may be emitted through a speaker 726 indicating to the user that the sterilization process is complete.

The writing instrument sterilizer 100 may be connected to a contaminant sensor 718 which senses and determines whether the writing instrument 102a is sufficiently sterilized. If the contaminant sensor 718 indicates that the writing instruments 102a are not sufficiently clean, the processor 720 will continue to instruct the power supply 728 to generate the UV light 170 until the contaminant sensor 718 detects and indicates a sterilized environment.

In more detail, the contaminant sensor 718 may be used to determine properties of the surface to be treated. Information of interest can include surface type, hardness, texture, reflectivity, and/or the extent of dirt and/or contaminants. Various other sensors, such as optical sensors, contact sensors, can be used to gather the information. The control circuit can give an indication of the surface properties and the information from the contaminant sensor 718 can be communicated to the processor 720 and used in a pre-programmed algorithm to adjust the UV intensity to be specifically tuned for the surface being treated. In the alternative, it may indicate that the UV light 170 should be moved closer to the surface of the writing instrument 8 and/or the UV intensity should be reduced.

The writing instrument sterilizer 100 may include safety sensors and interlocks (hereafter safety sensor 716) that shut off the UV light 170 when an unsafe condition is detected. An unsafe condition may include where a UV light 170 is directed away from the treatment surface and/or in directions where it can irradiate people or animals. If an unsafe situation should occur, the processor 720 will receive control signals from the safety sensor 66 noting the harmful environment, and the processor 720 will instruct the power supply 728 to cease its supply of power to the UV light 170.

In addition to the safety sensor or sensors 716, the design of the enclosure also prevents the escape of UV light from the enclosure. The design and location of both the collection aperture 130 and discharge aperture 140 in relation to the UV light 170 as well as the ejector member 300 help to prevent any UV light from escaping or emitting outside of the enclosure. Further, plastic doors may be attached in a hinged opening fashion to both the collection aperture 130 and discharge aperture 140 to provide additional UV protection.

In the alternative, an illumination switch 714 may be provided on the writing instrument sterilizer 100 which when activated, the processor 720 will instruct the irradiation of the UV light 170 until the inner compartment of the writing instrument sterilizer 100 is sterilized. When it has been determined that the writing instruments 8, are sterilized, the processor 720 will instruct the UV light 170 to cease operation.

The circuit includes controls for the ejector member 300 which may be controlled in a variety of different ways, including in response to a dispensing switch 712 and/or the input switch 710. If, for example, the dispensing switch 712 is activated, in response to the signal communicated to the processor 720, the processor 720 will instruct the power supply 728 to provide a source of power to motor 730 to drive the ejector member 300 through a cycle which would dispense a writing instrument.

The dispensing switch 712 may be embodied in a variety of different ways. For example, the dispensing switch 712 may be embodied as a motion or proximity switch, such that if the user motions his hand contemporaneously close to the dispensing switch 712 proximate the discharge aperture 140 located outside of the writing instrument sterilizer 100, the circuit will receive a control signal to dispense a writing instrument. The dispensing switch 712 may also be a touch sensor, a weight or location controlled switch working in conjunction with ejector member 300 or other element of sterilizer 100, a button that may be repressed and/or any other mode for activating a switch now known or later discovered in accordance with this invention. In the preferred embodiment, the present invention is able to determine that a sterilized writing instrument is not available in the dispensing frame 142 and automatically provides a new sterilized writing instrument to the dispensing frame 142 as a way of promoting the sterilization and recycling process of writing instruments.

In the alternative, the ejector member 300 may be instructed to cycle once and dispense a writing instrument in response to activation of the input switch 710. For example, if activation is sensed when a writing instrument 102a is inserted into the collection opening 130 or through switch/sensor 712, the processor 720 may issue an instruction to cycle the ejector member 300 to dispense a writing instrument. The writing instrument may be dispensed before or after the UV light 170 is activated to irradiate the various writing instruments. If, however, the only writing instrument in the writing instrument sterilizer 100 is the one recently deposited, the processor 720 will sterilize the writing instrument before it is dispensed for use.

It should be noted that the processor 720 may be preferably implemented as a central processor section having overall, system-level control, to performing various computations, functions and other processes related to the writing instrument sterilizer 100. The various components in the control circuit associated with the processor 720 can be implemented as a single microprocessor circuit or a plurality of separate dedicated or programmable integrated or other electronic circuits or devices, e.g., hardwired electronic or logic circuits such as discrete element circuits or programmable logic devices. The control circuit may include other circuitry or components, such as memory devices, relays, mechanical linkages, communications devices, etc., to affect desired control and/or input/output functions from various interfaces, such as where display 724 is an input/output interface. The writing instrument sterilizer 100 may include more than one controller for the various electronic components in accordance with this invention.

Programmable memory may be provided to receive and store the various data information and can also store one or more computer readable control routines used by the processor 720 to operate the writing instrument sterilizer 100. The memory can be implemented using any appropriate combination of alterable, volatile or non-volatile memory or non-alterable, or fixed, memory. The alterable memory, whether volatile or non-volatile, can be implemented using any one or more of static or dynamic RAM, floppy disk and disk drive, writable or re-writable optical disk and disk drive, hard drive, flash memory or the like. Similarly, the non-alterable or fixed memory can be implemented using any one or more of ROM, PROM, EPROM, EEPROM, an optical ROM disk, such as CD-ROM or DVD-ROM disk, and disk drive or the like.

While the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A writing instrument sterilizer system, comprising:
    a writing instrument, wherein the surface of the writing instrument forms at least one alignment indentation;
    a sterilizer comprising:
        a collection frame configured to receive the writing instrument,
        a discharge frame configured to dispense the writing instrument,
        a transport mechanism configured to transport the writing instrument from the collection frame to the discharge frame, and
        an illumination source that sterilizes the writing instrument by emitting radiation to the surface of the writing instrument; and
    wherein the sterilizer further comprising at least one alignment protrusion that engages and cooperates with the at least one alignment indentation of the writing instrument to maintain alignment of the writing instrument within the sterilizer.

2. The system of claim 1 wherein the surface of the writing instrument forms two alignment indentations.

3. The system of claim 1 wherein the surface of the writing instrument forms more than two alignment indentations.

4. The system of claim 1 wherein the transport mechanism comprises a carousel.

5. The system of claim 4 wherein the carousel comprises the at least one alignment protrusion.

6. The system of claim 1 wherein the transport mechanism comprises an ejector member.

7. The system of claim 1 wherein the collection frame comprises the at least one alignment protrusion.

8. The system of claim 1 wherein the discharge frame comprises the at least one alignment protrusion.

9. The system of claim 1 wherein track forms a plurality of protrusions, each protrusion cooperating with an indentation formed circumferentially around the longitudinal axis of the writing instrument.

10. The system of claim 1 wherein the geometry of the at least one alignment indentation corresponds with the geometry of the at least one alignment protrusion.

\* \* \* \* \*